(12) United States Patent
Miyamoto et al.

(10) Patent No.: US 11,386,983 B2
(45) Date of Patent: Jul. 12, 2022

(54) PRESERVING PRIVACY FOR DATA ANALYSIS

(71) Applicant: INTERNATIONAL BUSINESS MACHINES CORPORATION, Armonk, NY (US)

(72) Inventors: Kohtaroh Miyamoto, Tokyo (JP); Akira Koseki, Kanagawa-ken (JP)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 253 days.

(21) Appl. No.: 16/279,227

(22) Filed: Feb. 19, 2019

(65) Prior Publication Data
US 2020/0265929 A1    Aug. 20, 2020

(51) Int. Cl.
*G16H 10/60*    (2018.01)
*G06F 17/18*    (2006.01)
*G06F 21/62*    (2013.01)

(52) U.S. Cl.
CPC .............. *G16H 10/60* (2018.01); *G06F 17/18* (2013.01); *G06F 21/6245* (2013.01)

(58) Field of Classification Search
CPC .................. G06F 21/6245–6254; G06F 17/18
See application file for complete search history.

(56) References Cited

U.S. PATENT DOCUMENTS

| 2010/0100392 A1* | 4/2010 | Rothman | G16H 15/00 |
| | | | 705/2 |
| 2013/0339359 A1* | 12/2013 | Goyal | G06F 16/258 |
| | | | 707/737 |

(Continued)

FOREIGN PATENT DOCUMENTS

| EP | 2 879 069 | 6/2015 |
| EP | 3 046 044 | 7/2016 |
| WO | WO-2019200527 A1 * | 10/2019 ......... G06F 21/6254 |

OTHER PUBLICATIONS

M Widmann et al., Four Techniques for Outlier Detection, Oct. 1, 2018, KNIME (Year: 2018).*

(Continued)

*Primary Examiner* — Christopher L Gilligan
*Assistant Examiner* — Karen A Hranek
(74) *Attorney, Agent, or Firm* — Tutunjian & Bitetto, P.C.; Randall Bluestone

(57) ABSTRACT

A method is provided for anonymizing statistical data for a secure transfer. The method calculates statistical information for each of the statistical data. The method aggregates the statistical information to calculate a valid range for each of the statistical information. The method removes outlier data based on the valid range for each of the statistical data. The method creates pair lists from each of the statistical data and target data, the pair lists having a respective member from both the statistical data and the target data. The method replaces each respective member of the target data by a random number existing in a range of a corresponding one of a plurality of target data bins. The method swaps each pair in each pair list in a random order using the randomized number, wherein the random number used for swapping is different for different ones of the pair lists.

16 Claims, 10 Drawing Sheets

(56) References Cited

U.S. PATENT DOCUMENTS

| | | | | |
|---|---|---|---|---|
| 2015/0169895 A1* | 6/2015 | Gkoulalas-Divanis | ...................... | G06F 21/6254 726/26 |
| 2015/0302178 A1* | 10/2015 | Patel | ...................... | G16H 50/70 705/2 |
| 2017/0091391 A1* | 3/2017 | LePendu | .............. | G06F 21/6245 |
| 2017/0177798 A1* | 6/2017 | Samuel | ................ | G06F 21/6254 |
| 2017/0293892 A1 | 10/2017 | Kenthapadi | | |
| 2018/0232488 A1* | 8/2018 | Jafer | ................... | G06F 21/6254 |
| 2018/0358112 A1 | 12/2018 | Sharifi Sedeh et al. | | |
| 2020/0117833 A1* | 4/2020 | Pletea | .................... | G16H 70/60 |

OTHER PUBLICATIONS

Atreya et al., Reducing patient re-identification risk for laboratory results within research datasets, Jul. 21, 2021, J Am Med Inform Assoc 2013, 20:95-101 (Year: 2012).*

Zhang, Microdata Privacy Protection Through Permutation-Based Approaches, 2008 (Year: 2008).*

Li et al., Permutation Anonymization, Aug. 4, 2015, J Intell Inf Syst 47: 427-445 (Year: 2015).*

\* cited by examiner $800$

---

For each hospital (k=1,2,3,...), for each statistical data (A,B,C,...), calculate number ($N\_A_k$, $N\_B_k$, $N\_C_k$, ...), average ($\mu\_A_k, \mu\_B_k, \mu\_C_k, ...$), variance (average squared difference from average) ($\sigma\_A^2_k, \sigma\_B^2_k, \sigma\_C^2_k, ...$) and send to the analysis system.  — 805

↓ Statistical information of each statistical data

For each hospital data (k = 1, 2, 3, ...), aggregate the values and calculate the valid range of each statistical data and return (mina ~ maxA, etc.).
For example, for statistical data A, total number can be obtained as follows:

$$N_{A_{all}} = \sum_{k=1} N\_A_K$$

Similarly, the average for A is as follows:
$\mu\_A_{all} = \frac{1}{N\_A_{all}} \Sigma_{k=1} N_{A_k} * \mu\_A_k.$
The variance $\sigma$ is approximated as follows:

$$\sigma_{A_{all}} = \sqrt{\frac{1}{N\_A_{all}} \sum_{k=1} \sigma\_A_k^2 * N\_A_k}$$

This invention does not limit the criteria of the valid range but for example average $\pm 3\sigma$ can be applied to obtain minA, maxB as follows:

$$minA = \mu_{A_{all}} - 3 * \sigma\_A_{all}$$
$$maxA = \mu_{A_{all}} + 3 * \sigma\_A_{all}$$

— 810

↓

Output a valid range for each statistical data (minA, maxA, minB, maxB, etc.). — 815

FIG. 8

PRESERVING PRIVACY FOR DATA ANALYSIS

BACKGROUND

Technical Field

The present invention generally relates to data processing, and more particularly to preserving privacy for data analysis.

Description of the Related Art

It is an important task to analyze patient data (e.g., analyze several thousand statistical data and test (e.g., Welch's T-Test)) aggregated from multiple hospitals for diseases such as, for example, diabetes, cancer, and so forth against target data (e.g. HbA1c; average blood sugar level) and provide advice to prevent progressing of the disease. At the same time, it is required (by many standards and laws) to consider the privacy of the patient and the disclosure raw data is often an unacceptable situation. Hence, there is a need for an improved approach to preserving privacy for data analysis.

SUMMARY

According to an aspect of the present invention, a computer-implemented method is provided for anonymizing a plurality of statistical data for a secure transfer. The method includes calculating, by a hardware processor, statistical information for each of the plurality of statistical data. The method further includes aggregating, by the hardware processor, the statistical information to calculate a valid range for each of the statistical information. The method also includes removing, by the hardware processor, outlier data based on the valid range for each of the plurality of statistical data. The method additionally includes creating, by the hardware processor, pair lists from each of the plurality of statistical data and target data, the pair lists having a respective member from both the plurality of statistical data and the target data. The method further includes replacing, by the hardware processor, each respective member of the target data by a random number existing in a range of a corresponding one of a plurality of target data bins. The method also includes swapping, by the hardware processor, each pair in each of the pair lists in a random order using the randomized number, wherein the random number used for swapping is different for different ones of the pair lists.

According to another aspect of the present invention, a computer program product is provided for anonymizing a plurality of statistical data for a secure transfer. The computer program product includes a non-transitory computer readable storage medium having program instructions embodied therewith. The program instructions are executable by a computer to cause the computer to perform a method. The method includes calculating, by a hardware processor, statistical information for each of the plurality of statistical data. The method further includes aggregating, by the hardware processor, the statistical information to calculate a valid range for each of the statistical information. The method also includes removing, by the hardware processor, outlier data based on the valid range for each of the plurality of statistical data. The method additionally includes creating, by the hardware processor, pair lists from each of the plurality of statistical data and target data, the pair lists having a respective member from both the plurality of statistical data and the target data. The method further includes replacing, by the hardware processor, each respective member of the target data by a random number existing in a range of a corresponding one of a plurality of target data bins. The method also includes swapping, by the hardware processor, each pair in each of the pair lists in a random order using the randomized number, wherein the random number used for swapping is different for different ones of the pair lists.

According to yet another aspect of the present invention, a computer processing system is provided for anonymizing a plurality of statistical data for a secure transfer. The computer processing system includes a memory for storing program code. The computer processing system further includes a hardware processor for running the program code to calculate statistical information for each of the plurality of statistical data. The hardware processor further runs the program code to aggregate the statistical information to calculate a valid range for each of the statistical information. The hardware processor also runs the program code to remove outlier data based on the valid range for each of the plurality of statistical data. The hardware processor additionally runs the program code to create pair lists from each of the plurality of statistical data and target data, the pair lists having a respective member from both the plurality of statistical data and the target data. The hardware processor further runs the program code to replace each respective member of the target data by a random number existing in a range of a corresponding one of a plurality of target data bins. The hardware processor also runs the program code to swap each pair in each of the pair lists in a random order using the randomized number, wherein the random number used for swapping is different for different ones of the pair lists.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein:

FIG. 8 is a flow diagram showing an exemplary method for calculating a valid range of statistical data, in accordance with an embodiment of the present invention;

DETAILED DESCRIPTION

The present invention is directed to preserving privacy for data analysis.

In an embodiment, multiple collections of statistical and target data are secured for privacy preservation while each of the collections of statistical data can be statistically analyzed and the target data can be grouped together to test statistical significance to the statistical data.

In an embodiment, the present invention creates pairs of randomly swapped statistical data and target data and applies each pair list to a different random number. Also, the target data is randomized within a defined bin. These and other aspects of the present invention are described in further detail hereinbelow.

In an embodiment, the present invention can process statistical data and target data so that privacy information is not exposed, the target data is grouped (e.g., into 2 groups), and the statistical data is tested (e.g., by Welch's T-Test, retrieve p-value, etc.) to evaluate/determine whether there is a statistically significant difference. For example, the present invention can evaluate whether there is a statistically significant difference between a patient with high/low blood sugar level relative to a consumption speed of the meal.

Figure 1:
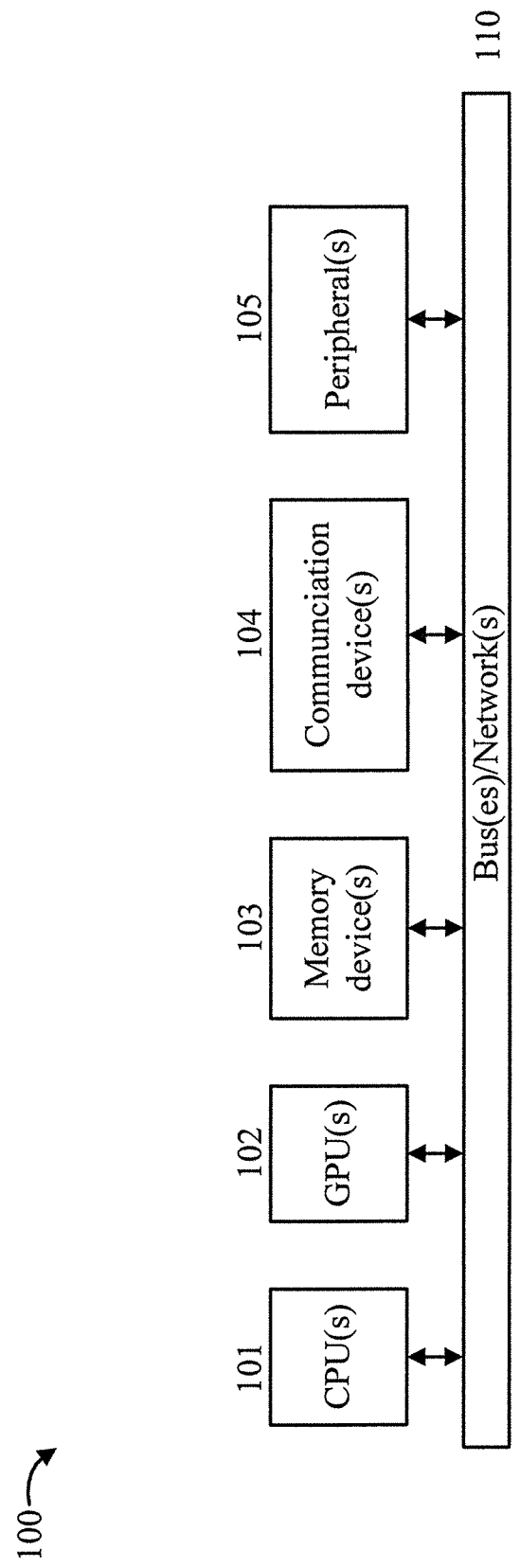
FIG. 1 is a block diagram showing an exemplary processing system to which the present invention may be applied, in accordance with an embodiment of the present invention.

FIG. 1 is a block diagram showing an exemplary processing system 100 to which the present invention may be applied, in accordance with an embodiment of the present invention. The processing system 100 includes a set of processing units (e.g., CPUs) 101, a set of GPUs 102, a set of memory devices 103, a set of communication devices 104, and set of peripherals 105. The CPUs 101 can be single or multi-core CPUs. The GPUs 102 can be single or multi-core GPUs. The one or more memory devices 103 can include caches, RAMs, ROMs, and other memories (flash, optical, magnetic, etc.). The communication devices 104 can include wireless and/or wired communication devices (e.g., network (e.g., WIFI, etc.) adapters, etc.). The peripherals 105 can include a display device, a user input device, a printer, an imaging device, and so forth. Elements of processing system 100 are connected by one or more buses or networks (collectively denoted by the figure reference numeral 110).

In an embodiment, memory devices 103 can store specially programmed software modules in order to transform the computer processor system in a special purpose computer configured to implement various aspects of the present invention. In an embodiment, special purpose hardware (e.g., Application Specific Integrated Circuits, and so forth) can be used to implement various aspects of the present invention.

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. Further, in another embodiment, a cloud configuration can be used (e.g., see FIGS. 9-10). These and other variations of the processing system 100 are readily contemplated by one of ordinary skill in the art given the teachings of the present invention provided herein.

Moreover, it is to be appreciated that various figures as described below with respect to various elements and steps relating to the present invention that may be implemented, in whole or in part, by one or more of the elements of system 100.

Figure 2:
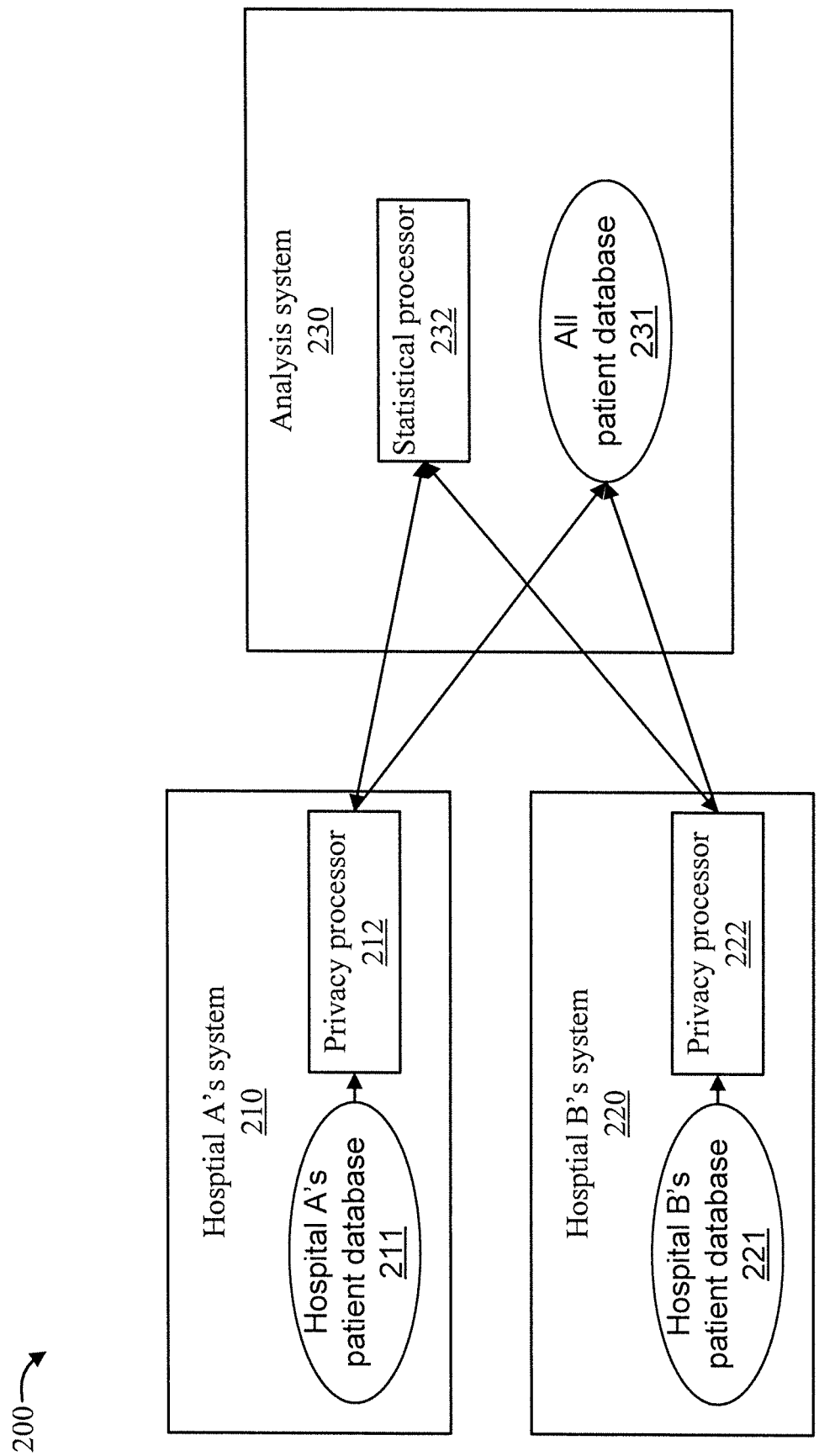
FIG. 2 is a block diagram showing an exemplary environment to which the present invention can be applied, in accordance with an embodiment of the present invention.

FIG. 2 is a block diagram showing an exemplary environment 200 to which the present invention can be applied, in accordance with an embodiment of the present invention.

The environment 200 includes a hospital A system 210, a hospital B system 220, and an analysis system 230.

The hospital A system 210 includes hospital A patient database 211 and a privacy processor 212.

The hospital B system 220 includes hospital B patient database 221 and a privacy processor 222.

The analysis system 230 includes all patients database 231 and a statistical processor 232.

Figure 3:
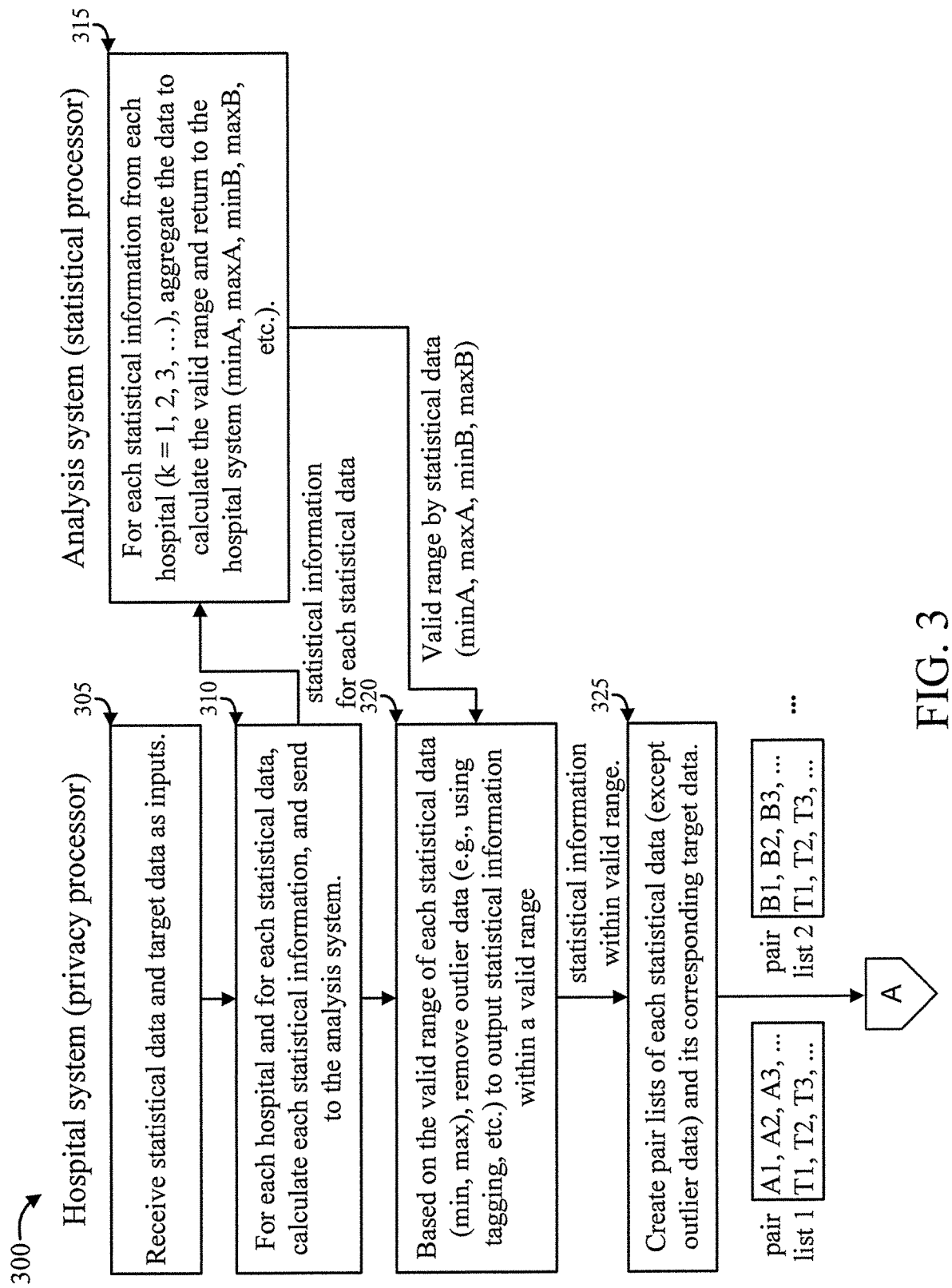
FIGS. 3-5 are high-level block diagrams showing an exemplary process/system for preserving privacy for data analysis, in accordance with an embodiment of the present invention.
Figure 4:
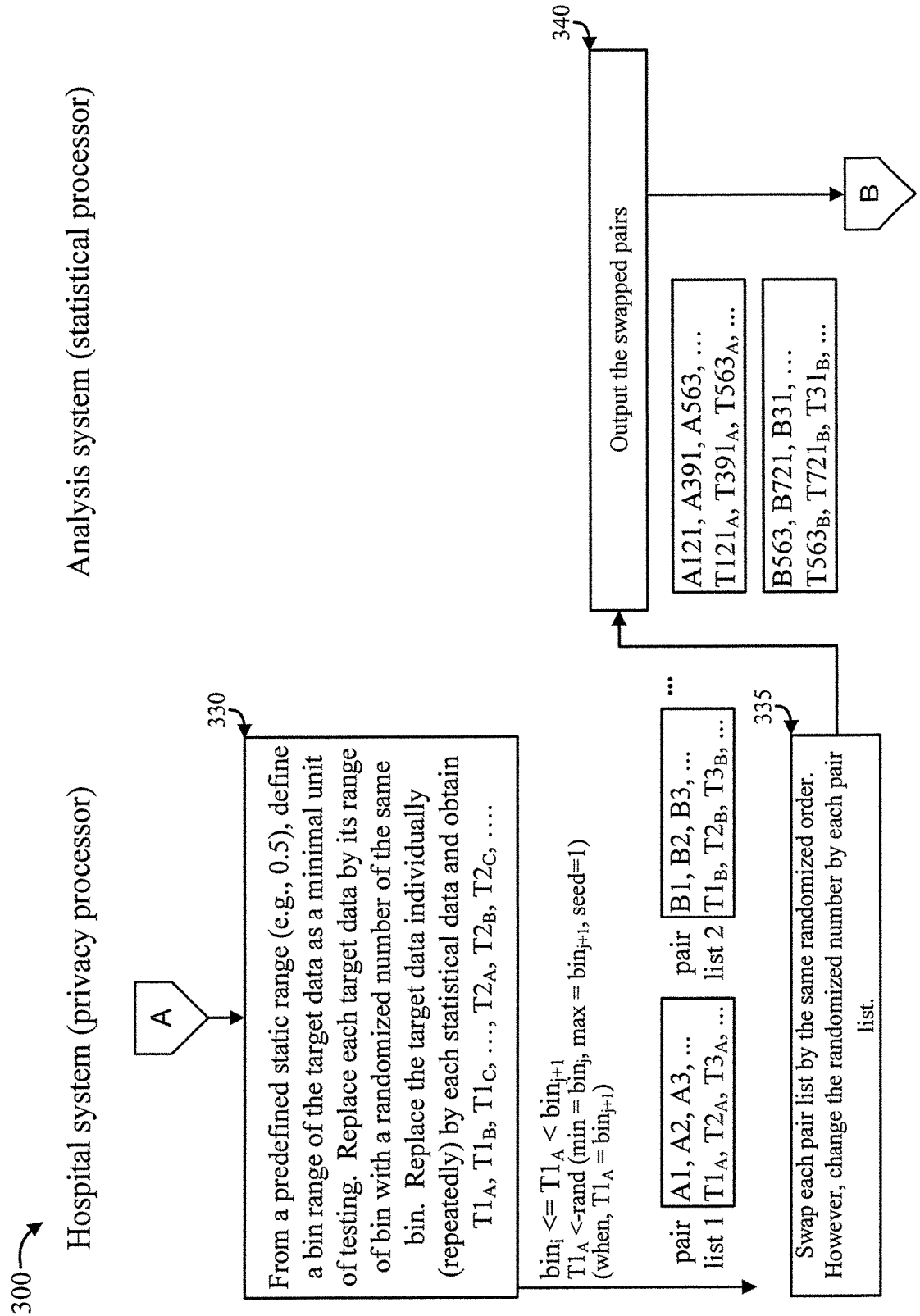
Figure 5:
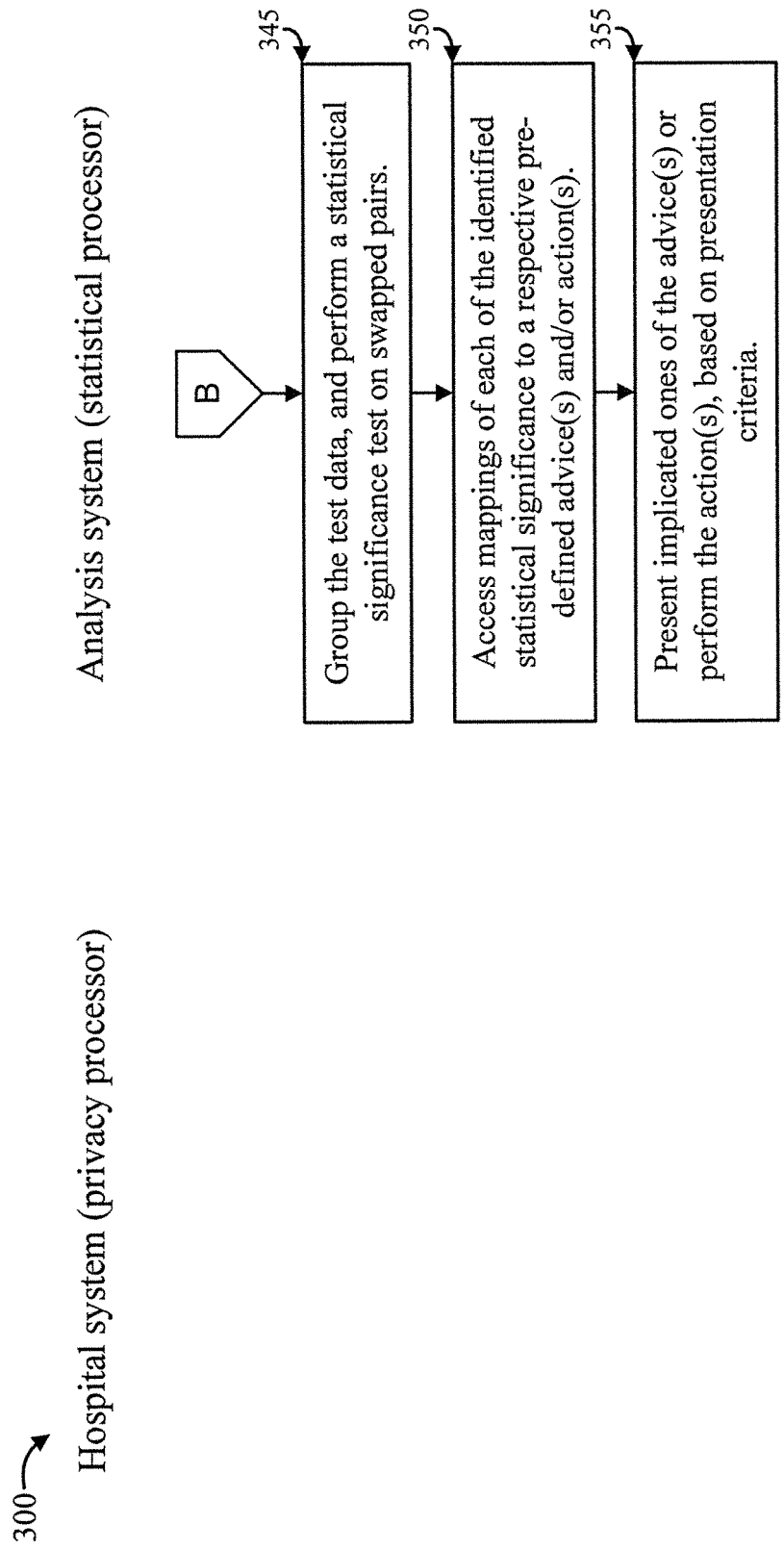

FIGS. 3-5 is a high-level block diagram showing an exemplary process/system 300 for preserving privacy for data analysis, in accordance with an embodiment of the present invention.

In FIGS. 3-5, the left side corresponds to a hospital or other entity system, and the right side corresponds to an analysis system.

At block 305, receive statistical data and target data as inputs.

The statistical data can include, but is not limited to, the following:

| Meal amount | $A = \{A1, A2, A3, \ldots\}$ |
| Meal speed | $B = \{B1, B2, B3, \ldots\}$ |
| Meal frequency | $C = \{C1, C2, C3, \ldots\}$ |
| Exercise frequency | $D = \{D1, D2, D3, \ldots\}$ |
| White rice amount | $E = \{E1, E2, E3, \ldots\}$ |

Etc.

The target data can include, but is not limited to, the following:

| HbA1c | $T = \{T1, T2, T3, \ldots\}$ |

At block 310, for each hospital and for each statistical data, calculate each statistical information (e.g., number, average, variance), and send to the analysis system. Thus, statistical information for each statistical data is sent to the analysis system.

At block 315, for each statistical information from each hospital (k=1, 2, 3, . . . ), aggregate the data to calculate the valid range and return to the hospital system (minA, maxA, minB, maxB, etc.). Thus, valid ranges by statistical data (minA, maxA, minB, maxB) can be provided.

At block 320, based on the valid range of each statistical data (min, max), remove outlier data to output statistical information within a valid range. Outlier data can be removed using a method including, but not limited to, for example, tagging.

At block 325, create pair lists of each statistical data (except outlier data) and its corresponding target data. It is noted that block 325 specifically uses the target data that corresponds to each statistical data in order to maintain the relationship between the statistical data and the target data.

In an embodiment, block 325 can involve pair list 1 and pair list 2 as shown.

At block 330, from a predefined static range (e.g., 0.5), define a bin range of the target data as the minimal unit of testing. This will eliminate the risk of exposing a specific patient by its unique target data. For example, in HbA1c, 7 bins (under 6.5, 6.5 through 7, 7 through 7.5, 7.5 through 8, 8 through 8.5, 8.5 through 9/9, and above) maybe defined. In this case, grouping for statistical testing maybe performed at any of the 6 boundaries of the bin (6.5, 7, 7.5, 8, 8.5, 9). Replace each target data by its range of bin with a randomized number of the same bin. For example, if the bin is 0.5 and T1 is 8.6, then replace the data with randomized data within 8.5 and 9.0. Replace the target data individually (repeatedly) by each statistical data and obtain $T1_A$, $T1_B$, $T1_C$, ..., $T2_A$, $T2_B$, $T2_C$, Hence, as an example, the following can apply with respect to block 330:

When $Bin_j <= T1 < bin_{j+1}$
$T1_A$=rand (min=$bin_j$, max=$bin_{j+1}$, seed=1)
(where, $T1_A$=$bin_{j+1}$)

In this way, modified pair list 1 and modified pair list 2 can be obtained.

At block 335, swap each pair list by the same randomized order. However, change the randomized number by each pair list. In this way, each statistical data can be analyzed by forming 2 groups of target data and testing each statistical data.

At block 340, send the swapped pairs over a communication path (e.g.., wired and/or wireless) for secure transfer At block 345, group the test data, and perform a statistical significance test on swapped pairs.

At block 350, access mappings of each of the identified statistical significance to a respective pre-defined advice(s) and/or action(s).

At block 355, present implicated ones of the advice(s) or perform the action(s), based on presentation criteria. For example, the presentation criteria can include the statistical relevance being greater than a threshold amount.

A description will now be given regarding various applications and use examples to which the present invention can be applied, in accordance with one or more embodiments of the present invention.

As one example, list all the statistical data with a significant difference, and provide advice (and/or actions) based on such listed items. For example, if the amount of eaten raw fish is significantly high for HbA1c low groups, then one may advise, for example, on a display screen or an audio reproduction device (e.g., a speaker), the following: "It is good to eat raw fish to lower the HbA1c values". This can be performed either on the data system (e.g., hospital side) or analysis system (analysis side).

While the case of hospital patient data is shown, the present invention can be readily applied to studying, sports, music and other skill areas to show which statistical data is significant in raising one's skill level, as readily appreciated by one of ordinary skill in the art, given the teachings of the present invention provided herein.

Figure 6:
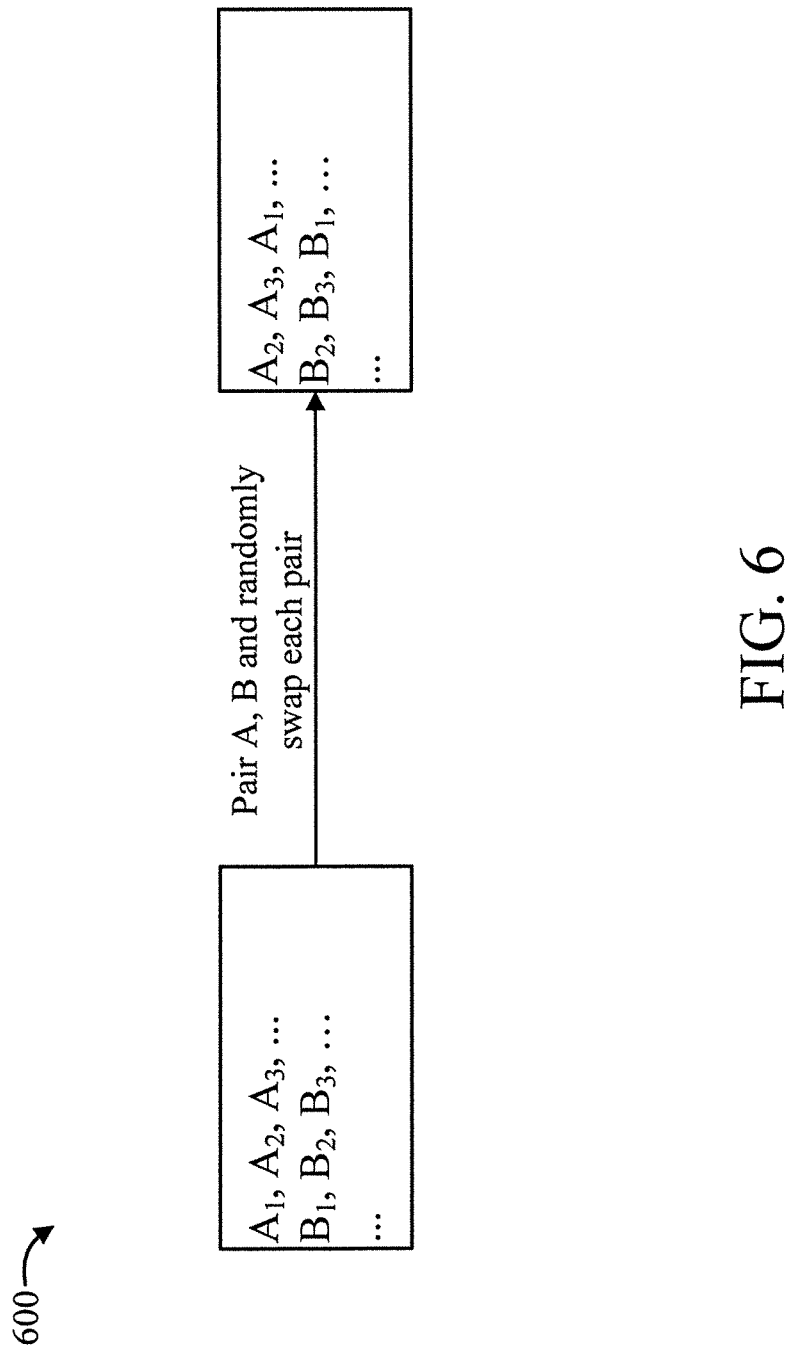
FIG. 6 is a block diagram showing exemplary randomly swapped pairs A and B, in accordance with an embodiment of the present invention.

As another case, the present invention can be used to calculate the correlation between one statistical data with another (e.g. correlation value). This patent can be simply applied by pairing such data. For example, if it is required to calculate the correlation between A (A1, A2, A3, . . . ) and B (B1, B2, B3, . . . ) apply the same techniques explained beforehand between A (A1, A2, A3, . . . ) and T (T1, T2, T3, . . . ) and create a pair list between each statistical data of A and B swap each pair list. FIG. 6 is a block diagram showing exemplary randomly swapped pairs 600 A and B, in accordance with an embodiment of the present invention.

Figure 7:
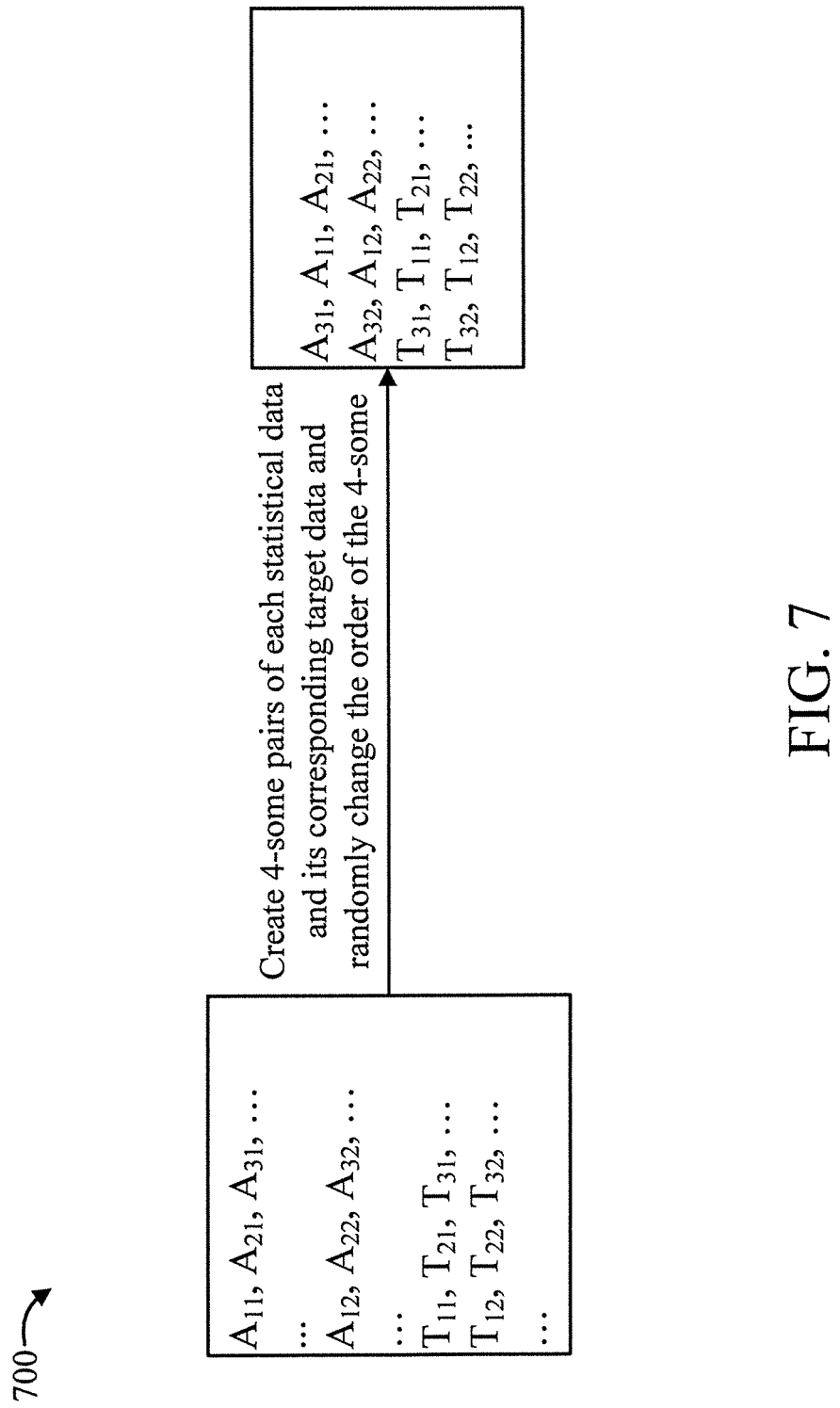
FIG. 7 is a block diagram showing exemplary 4-some pairs to which the present invention can be applied, in accordance with an embodiment of the present invention.

As yet another case, the present invention can be used to take 2 snapshots and analyze how the difference of the value is significant to the difference in the target information, then simply create 4-some pairs and follow the same procedures. FIG. 7 is a block diagram showing exemplary 4-some pairs 700 to which the present invention can be applied, in accordance with an embodiment of the present invention.

FIG. 8 is a flow diagram showing an exemplary method 800 for calculating a valid range of statistical data, in accordance with an embodiment of the present invention. Block 805 corresponds to a hospital side (privacy processor), and blocks 810 and 815 correspond to the analysis system side (statistical processor).

At block 805, for each hospital (k=1, 2, 3, . . . ), for each statistical data (A, B, C, . . . ), calculate number ($N\_A_k$, $N\_B_k$, $N\_C_k$, . . . ), average ($\mu\_A_k$, $\mu\_B_k$, $\mu\_C_k$, . . . ), variance (average squared difference from average) ($\sigma\_A^2_k$, $\sigma\_B^2_k$, $\sigma\_C^2_k$, . . . ), and send to the analysis system.

At block 810, for each hospital data (k=1, 2, 3, . . . ), aggregate the values and calculate the valid range of each statistical data and return (mina~maxA, etc.).

For example, for statistical data A, total number can be obtained as follows:

$$N\_A_{all} = \sum_{k=1} N\_A_K$$

Similarly, the average for A is as follows:

$$\mu\_A_{all} = \frac{1}{N\_A_{all}} \sum_{k=1} N_{A_k} * \mu\_A_k.$$

The variance σ is approximated as follows:

$$\sigma\_A_{all} = \sqrt{\frac{1}{N\_A_{all}} \sum_{k=1} \sigma\_A_k^2 * N\_A_k}$$

This invention does not limit the criteria of the valid range but for example average ±3σ can be applied to obtain minA, maxB as follows:

$minA = \mu_{A_{all}} - 3 * \sigma\_A_{all}$ $maxA = \mu_{A_{all}} + 3 * \sigma\_A_{all}$ At block 815, output a valid range for each statistical data (minA, maxA, minB, maxB, etc.).

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 9:
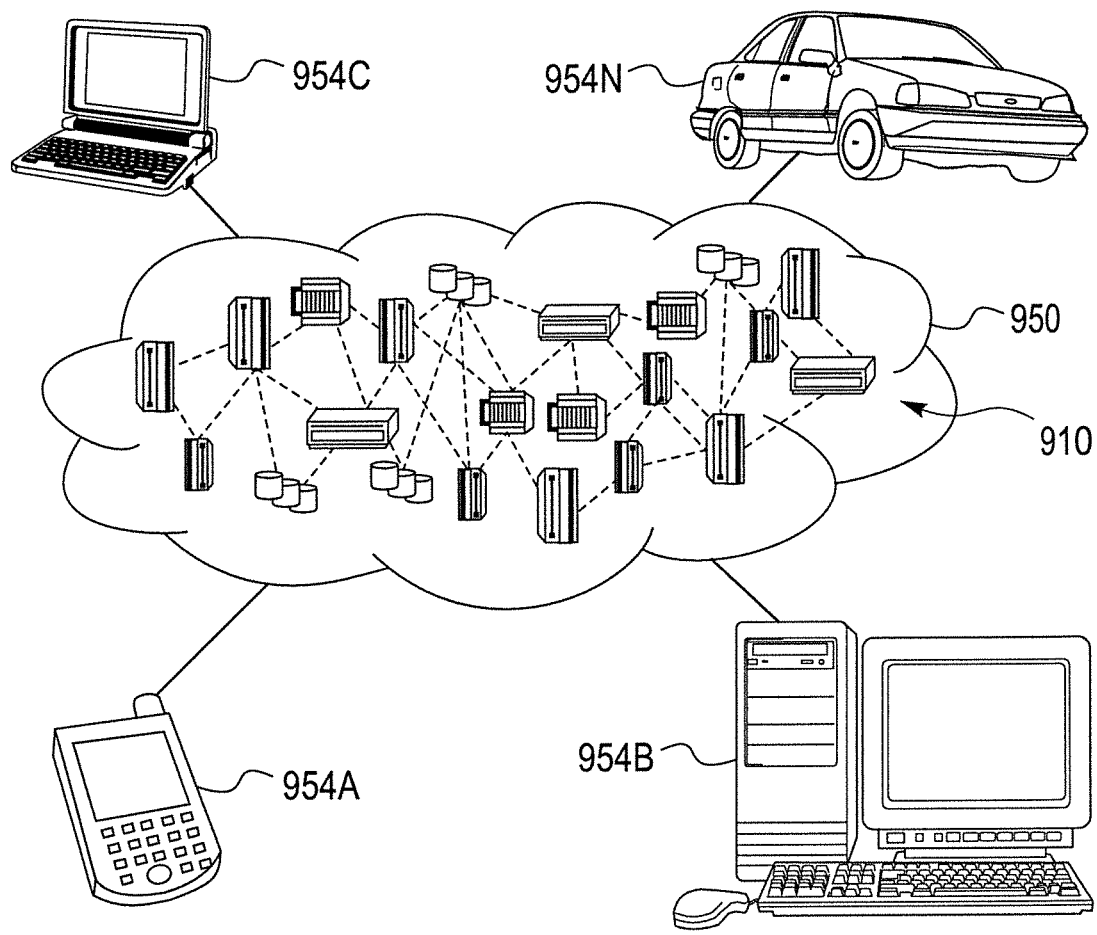
FIG. 9 is a block diagram showing an illustrative cloud computing environment having one or more cloud computing nodes with which local computing devices used by cloud consumers communicate, in accordance with an embodiment of the present invention.

Referring now to FIG. 9, illustrative cloud computing environment 950 is depicted. As shown, cloud computing environment 950 includes one or more cloud computing nodes 910 with which local computing devices used by cloud consumers, such as, for example, personal digital assistant (PDA) or cellular telephone 954A, desktop computer 954B, laptop computer 954C, and/or automobile computer system 954N may communicate. Nodes 910 may communicate with one another. They may be grouped (not shown) physically or virtually, in one or more networks, such as Private, Community, Public, or Hybrid clouds as described hereinabove, or a combination thereof. This allows cloud computing environment 950 to offer infrastructure, platforms and/or software as services for which a cloud consumer does not need to maintain resources on a local computing device. It is understood that the types of computing devices 954A-N shown in FIG. 9 are intended to be illustrative only and that computing nodes 910 and cloud computing environment 950 can communicate with any type of computerized device over any type of network and/or network addressable connection (e.g., using a web browser).

Figure 10:
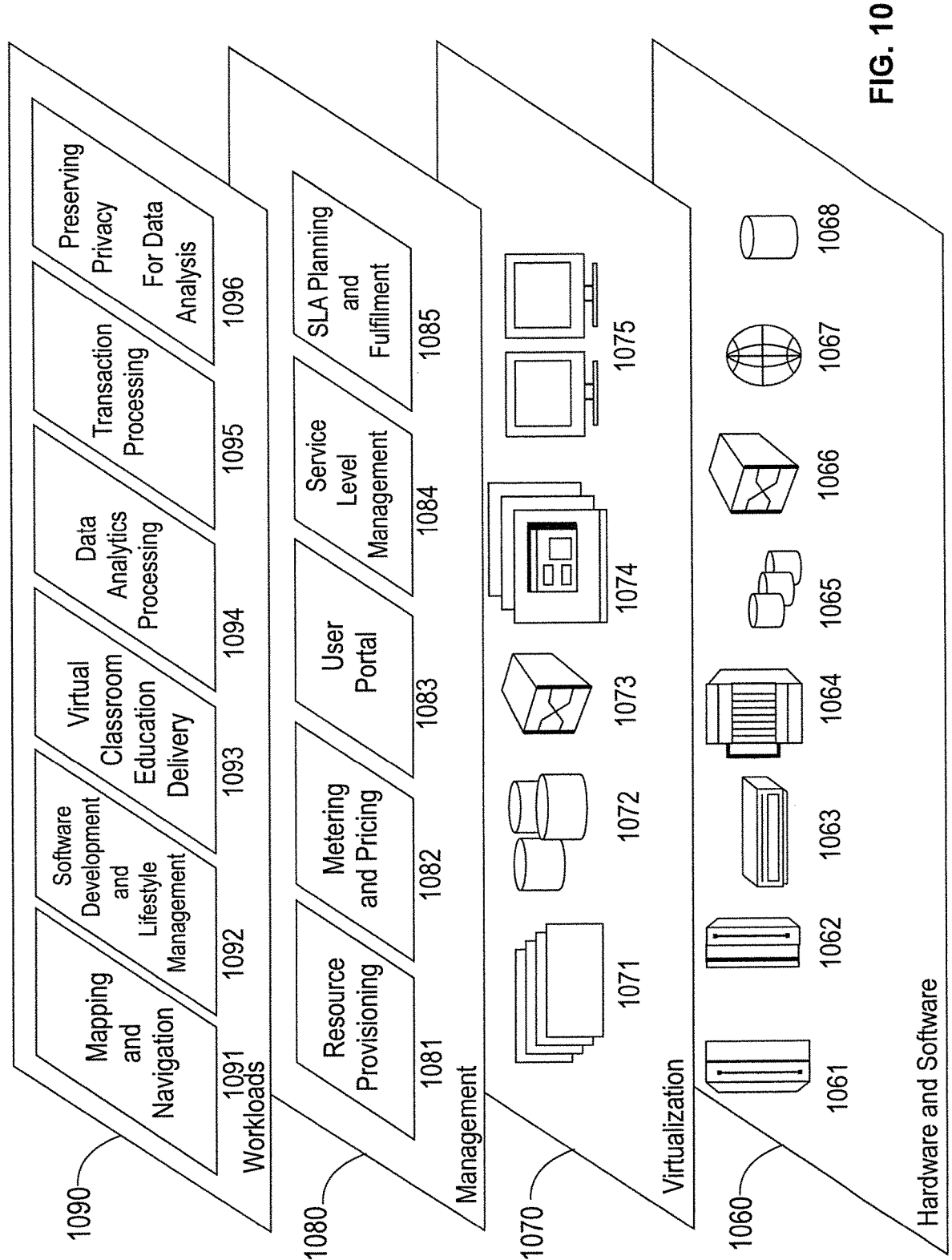
FIG. 10 is a block diagram showing a set of functional abstraction layers provided by a cloud computing environment, in accordance with an embodiment of the present invention.

Referring now to FIG. 10, a set of functional abstraction layers provided by cloud computing environment 950 (FIG. 9) is shown. It should be understood in advance that the components, layers, and functions shown in FIG. 10 are intended to be illustrative only and embodiments of the invention are not limited thereto. As depicted, the following layers and corresponding functions are provided:

Hardware and software layer 1060 includes hardware and software components. Examples of hardware components include: mainframes 1061; RISC (Reduced Instruction Set Computer) architecture based servers 1062; servers 1063; blade servers 1064; storage devices 1065; and networks and networking components 1066. In some embodiments, software components include network application server software 1067 and database software 1068.

Virtualization layer 1070 provides an abstraction layer from which the following examples of virtual entities may be provided: virtual servers 1071; virtual storage 1072; virtual networks 1073, including virtual private networks; virtual applications and operating systems 1074; and virtual clients 1075.

In one example, management layer 1080 may provide the functions described below. Resource provisioning 1081 provides dynamic procurement of computing resources and other resources that are utilized to perform tasks within the cloud computing environment. Metering and Pricing 1082 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 1083 provides access to the cloud computing environment for consumers and system administrators. Service level management 1084 provides cloud computing resource allocation and management such that required service levels are met. Service Level Agreement (SLA) planning and fulfillment 1085 provide pre-arrangement for, and procurement of, cloud computing resources for which a future requirement is anticipated in accordance with an SLA.

Workloads layer 1090 provides examples of functionality for which the cloud computing environment may be utilized. Examples of workloads and functions which may be provided from this layer include: mapping and navigation 1091; software development and lifecycle management 1092; virtual classroom education delivery 1093; data analytics processing 1094; transaction processing 1095; and preserving privacy for data analysis 1096.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A computer-implemented method for anonymizing a plurality of statistical data for a secure transfer, the method comprising:
   calculating, by each of a plurality of privacy processors managing access to a plurality of isolated patient databases of a plurality of hospital computer processing systems, statistical information for each of the plurality of statistical data for a patient, the privacy processors being respective portals through which the statistical data is anonymized for the secure transfer, each of the plurality of privacy processors connected to a respective one of the plurality of isolated patient databases of a respective one of the plurality of hospital computer processing systems;
   aggregating, by the plurality of privacy processors, the statistical information;
   creating, by the plurality of privacy processors, pair lists from each of the plurality of statistical data and target data, the pair lists having a respective member from both the plurality of statistical data and the target data, the target data relating to a specific health status test;
   replacing, by the plurality of privacy processors, each respective member of the target data by a random number existing in a range of a corresponding one of a plurality of target data bins defined from a predefined static range;
   swapping, by the plurality of privacy processors, each pair in each of the pair lists in a random order using a randomized number, wherein the randomized number used for swapping is different for different ones of the pair lists;
   performing, by a wireless communication device, the secure transfer for patient privacy protection, by sending the swapped pairs over multiple communication paths from the plurality of hospital computer processing systems to a remote statistical analysis system, wherein the wireless communication device transforms the swapped pairs into a wireless signal; and
   performing, by a statistical processor, a statistical significance test on the swapped pairs at the remote statistical analysis system.

2. The computer-implemented method of claim 1, wherein each of the plurality of bins is defined based on the predefined static range for each of the plurality of target data calculated according to a target data analytical purpose.

3. The computer-implemented method of claim 1, further comprising securely storing the plurality of statistical data and the target data for privacy preservation.

4. The computer-implemented method of claim 1, further comprising:
   statistically analyzing the plurality of statistical data; and
   grouping test data and testing a corresponding statistical significance of the test data with respect to each of the plurality of statistical data.

5. The computer-implemented method of claim 4, further comprising:
   mapping each of the plurality of statistical data to a respective one of a plurality of pre-defined advices of user action for overcoming a health deficiency; and
   presenting, on a display device, implicated ones of the plurality of pre-defined advices to a user to prevent disease progression, based on presentation criteria.

6. The computer-implemented method of claim 4, further comprising filtering results of the testing based on statistical significance.

7. The computer-implemented method of claim 1, wherein the statistical information comprises a number of occurrences, an average, and a variance.

8. A computer program product for anonymizing a plurality of statistical data for a secure transfer, the computer program product comprising a non-transitory computer readable storage medium having program instructions embodied therewith, the program instructions executable by a hospital computer processing system to cause the hospital computer processing system to perform a method comprising:

calculating, by each of a plurality of privacy processors managing access to a plurality of isolated patient databases of a plurality of hospital computer processing systems, statistical information for each of the plurality of statistical data for a patient, the privacy processors being respective portals through which the statistical data is anonymized for the secure transfer, each of the plurality of privacy processors connected to a respective one of the plurality of isolated patient databases of a respective one of the plurality of hospital computer processing systems;

aggregating, by the plurality of privacy processors, the statistical information to calculate a valid range for each of the statistical data;

removing, by the plurality of privacy processors, outlier data based on the valid range for each of the plurality of statistical data;

creating, by the plurality of privacy processors, pair lists from each of the plurality of statistical data and target data, the pair lists having a respective member from both the plurality of statistical data and the target data, the target data relating to a specific health status test;

replacing, by the plurality of privacy processors, each respective member of the target data by a random number existing in a range of a corresponding one of a plurality of target data bins;

swapping, by the plurality of privacy processors, each pair in each of the pair lists in a random order using a randomized number, wherein the randomized number used for swapping is different for different ones of the pair lists;

performing, by a wireless communication device, the secure transfer for patient privacy protection, by sending the swapped pairs over multiple communication paths from the plurality of hospital computer processing systems to a remote statistical analysis system, wherein the wireless communication device transforms the swapped pairs into a wireless signal; and performing, by a statistical processor, a statistical significance test on the swapped pairs at the remote statistical analysis system.

9. The computer program product of claim 8, wherein each of the plurality of bins is defined based on the pre-defined static range for each of the plurality of target data calculated according to a target data analytical purpose.

10. The computer program product of claim 8, wherein the method further comprises securely storing the plurality of statistical data and the target data for privacy preservation.

11. The computer program product of claim 8, wherein the method further comprises:
statistically analyzing the plurality of statistical data; and
grouping test data and testing a corresponding statistical significance of the test data with respect to each of the plurality of statistical data.

12. The computer program product of claim 11, wherein the method further comprises:
mapping each of the plurality of statistical data to a respective one of a plurality of pre-defined advices of user action for overcoming a health deficiency; and
presenting, on a display device, implicated ones of the plurality of pre-defined advices to a user to prevent disease progression, based on presentation criteria.

13. The computer program product of claim 11, wherein the method further comprises filtering results of the testing based on statistical significance.

14. The computer program product of claim 8, wherein the statistical information comprises a number of occurrences, an average, and a variance.

15. The computer program product of claim 14, wherein the valid range comprises a minimum value and a maximum value.

16. A system for anonymizing a plurality of statistical data for a secure transfer, the system comprising:
a memory device for storing program code;
a plurality of isolated patient databases in a plurality of hospital computer processing systems for storing the plurality of statistical data; and
a plurality of privacy processors, each connected to a respective one of the plurality of isolated patient databases of a respective one of the plurality of hospital computer processing systems for running the program code and providing managing access to the respective one of the plurality of isolated patient databases to
calculate statistical information for each of the plurality of statistical data for a patient;
aggregate the statistical information;
create pair lists from each of the plurality of statistical data and target data, the pair lists having a respective member from both the plurality of statistical data and the target data, the target data relating to a specific health status test;
replace each respective member of the target data by a random number existing in a range of a corresponding one of a plurality of target data bins;
swap each pair in each of the pair lists in a random order using a randomized number, wherein the randomized number used for swapping is different for different ones of the pair lists; and
a wireless communication device for
performing the secure transfer for patient privacy protection by sending the swapped pairs over multiple communication paths from the plurality of hospital computer processing systems to a remote statistical analysis system, wherein the wireless communication device transforms the swapped pairs into a wireless signal;
wherein a statistical processor performs a statistical significance test on the swapped pairs at the remote statistical analysis system.

* * * * *